United States Patent [19]
Ohi et al.

[11] 3,975,395
[45] Aug. 17, 1976

[54] ARYL-TETRAZOL-5-YLTHIO- AND THIOETHER-SUBSTITUTED HYDROQUINONE COMPOUNDS

[75] Inventors: Reiichi Ohi; Tadao Shishido, Minami-ashigara, Japan

[73] Assignee: Fuji Photo Film Co., Ltd., Minami-ashigara, Japan

[22] Filed: Dec. 19, 1974

[21] Appl. No.: 534,394

[30] Foreign Application Priority Data
Dec. 19, 1973 Japan............................ 48-143291

[52] U.S. Cl............................................ 260/308 D
[51] Int. Cl.².......................................... C07D 257/04
[58] Field of Search........................... 260/308 D

[56] References Cited
UNITED STATES PATENTS
3,379,529  4/1968  Porter et al............................ 96/36

*Primary Examiner*—Frederick E. Waddell
*Attorney, Agent, or Firm*—Sughrue, Rothwell, Mion, Zinn & Macpeak

[57] ABSTRACT

Tri-substituted hydroquinone compounds having an aryl-tetrazol-5-ylthio group and at least one thioether group useful as photographic additives.

3 Claims, 2 Drawing Figures

ARYL-TETRAZOL-5-YLTHIO- AND THIOETHER-SUBSTITUTED HYDROQUINONE COMPOUNDS

BACKGROUND OF THE INVENTION

1. Field of the Invention

The present invention relates to hydroquinone compounds. Particularly, it relates to novel tri-substituted hydroquinone compounds having an aryl-tetrazol-5-ylthio group and at least one thioether group.

2. Description of the Prior Art

It is well known that 2-(1-aryl-5-tetrazolylthio)hydroquinone releases a 1-aryl-5-tetrazolylthio group in the presence of an alkali and an oxidized product of a p-phenylenediamine compound. This 1-aryl-5-tetrazolylthio group has been called a development inhibitor, because this group has a function of inhibiting the development of photographic sensitive materials. Further, 2-(1-aryl-5-tetrazolylthio)-hydroquinone has been called a development inhibitor releasable hydroquinone (hereinafter described as a DIR-hydroquinone), because it releases a development inhibitor at color development. U.S. Pat. Nos. 3,364,022, 3,379,529, 3,620,746 and 3,639,417 disclose that 2-(1-phenyl-5-tetrazolylthio)-hydroquinone derivatives can be utilized in photographic materials.

However, the DIR-hydroquinone derivatives described in these prior patents do not presently provide sufficient photographic properties, and thus it has been desired to find compounds which provide improved photographic properties.

SUMMARY OF THE INVENTION

Accordingly, a first object of the present invention is to provide hydroquinone compounds.

A second object of the present invention is to provide hydroquinone compounds which provide excellent photographic properties.

A third object of the present invention is to provide novel tri-substituted hydroquinone compounds.

As the result of much research and testing in order to attain the above described objects, novel tri-substituted hydroquinone compounds providing excellent photographic effects have now been discovered.

The novel tri-substituted hydroquinone compounds of the present invention are represented by the general formula (I)

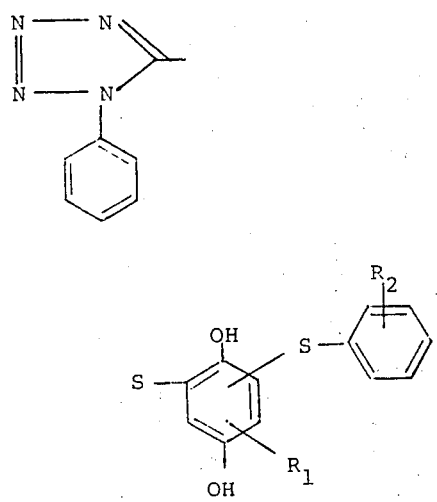

(I)

wherein $R_1$ represents an alkyl group having 6 or more carbon atoms or an alkylthio group having 6 or more carbon atoms, and $R_2$ represents a hydrogen atom, an alkyl group, a nitro group, a carboxylic acid group or an alkoxycarbonyl group.

Figure 1:
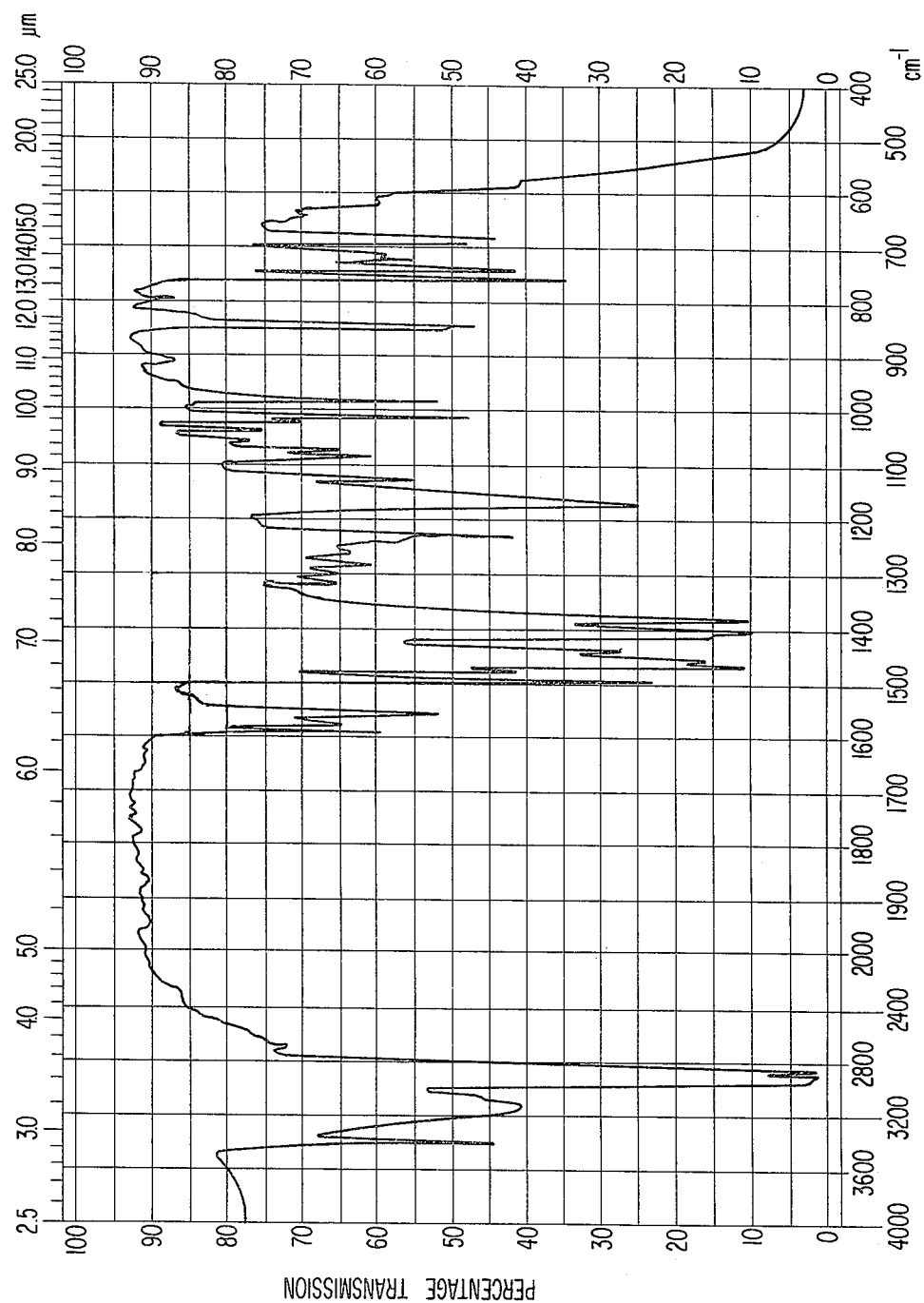
FIG. 1 shows the infrared absorption spectrum of 2-n-octadecylthio-5-(1-phenyl-5-tetrazolylthio)-6-phenylthiohydroquinone synthesized in Example 2.
Figure 2:
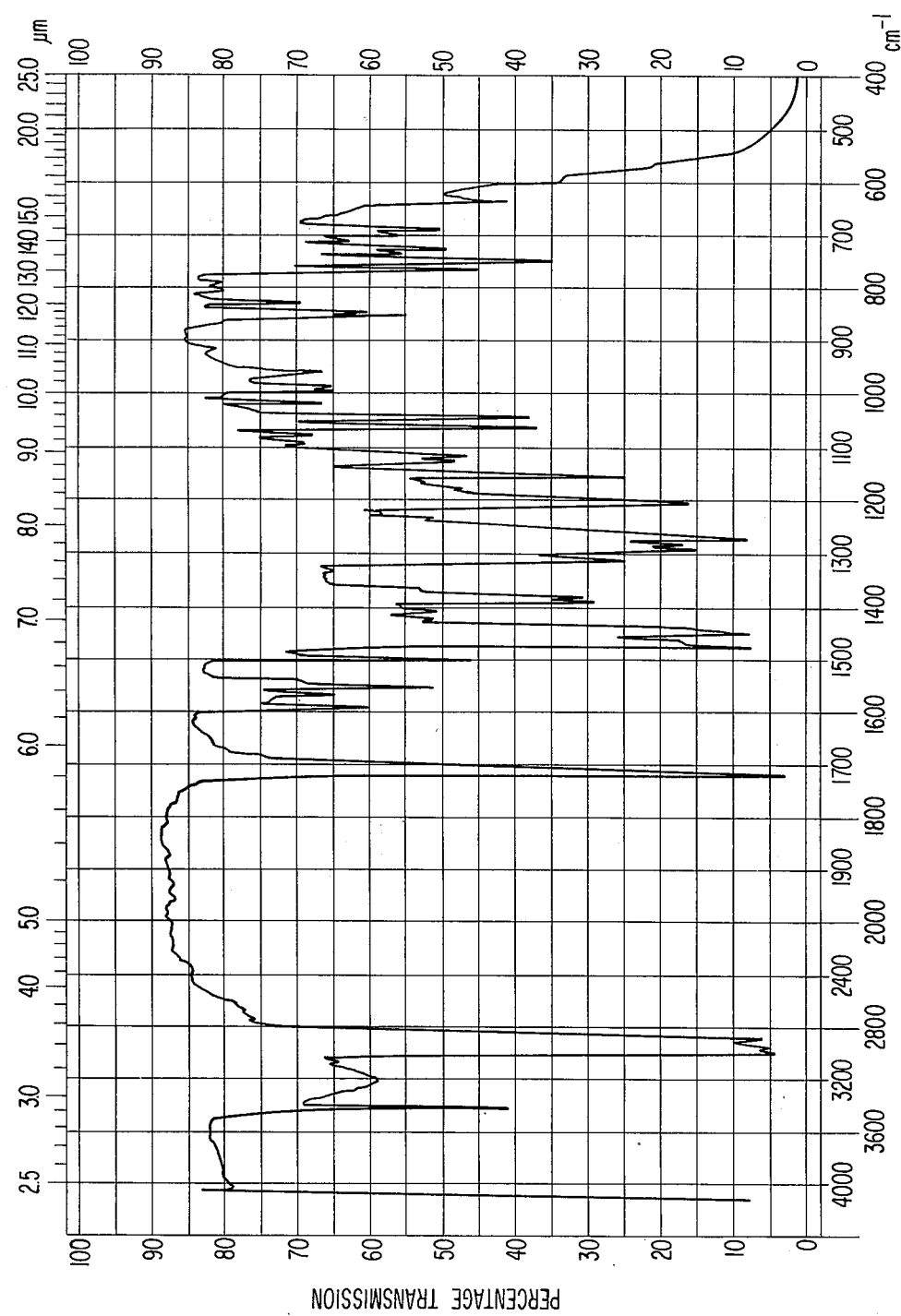
FIG. 2 shows the infrared absorption spectrum of 2-(2,5-dihydroxy-3-n-octadecylthio-6-(1-phenyl-5-tetrazolylthio))-phenylthiobenzoic acid methyl ester synthesized in Example 4.

The determination in FIGS. 1 and 2 was carried out by dispersing the compound in liquid paraffin, placing the sample between sodium chloride plates and measuring the infrared absorption spectrum using an IRA-a type infrared spectrophotometer produced by Nihon Bunko Co.

DETAILED DESCRIPTION OF THE INVENTION

The compounds of the present invention can be synthesized using well known techniques. Namely, the novel tri-substituted hydroquinone compounds of the present invention are produced by reacting a di-substituted benzoquinone having the general formula (II) with a thiol compound having the general formula (III) according to the following reaction schematic.

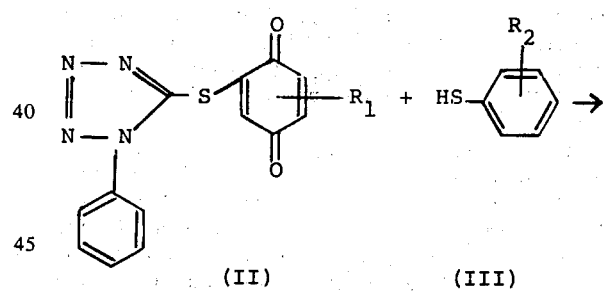

(II)          (III)

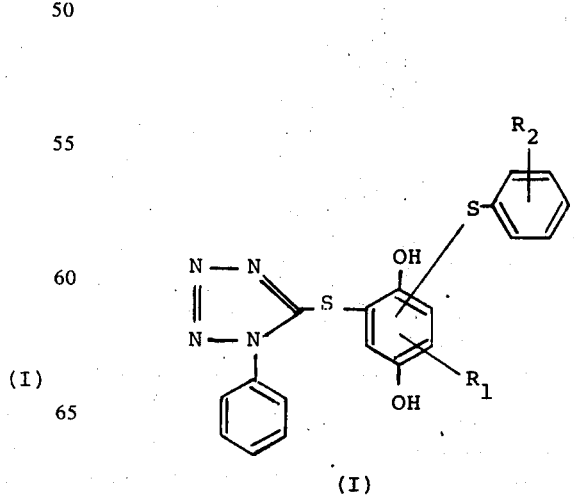

(I)

wherein $R_1$ and $R_2$ are as described above.

In the above described general formulae, $R_1$ is an alkyl group having 6 or more carbon atoms, e.g., having up to about 18 carbon atoms, or an alkylthio group having 6 or more carbon atoms, e.g., up to about 18 carbon atoms. Suitable examples of alkyl groups for $R_1$ are a hexyl, octyl, decyl, dodecyl, pentadecyl, hexadecyl, octadecyl, etc., groups, and suitable examples of alkylthio groups are thio groups substituted with the above described alkyl groups. $R_2$ is a hydrogen atom, an alkyl group, e.g., having 1 to 5 carbon atoms such as a methyl, ethyl propylbutyl, or pentyl group, a nitro group, a carboxylic acid group or an alkoxycarbonyl group, e.g., having 1 to 18 carbon atoms in the alkyl moiety thereof such as a methoxycarbonyl, ethoxycarbonyl, propoxycarbonyl, butoxycarbonyl, pentoxycarbonyl, hexoxycarbonyl, octoxycarbonyl, decoxycarbonyl, dodecoxycarbonyl, pentadecoxycarbonyl, hexadecoxycarbonyl, octadecoxycarbony, etc., group One of the starting materials is a di-substituted benzoquinone having the general formula (II) and particularly a di-substituted p-benzoquinone, wherein a 1-aryl-5-tetrazolylthio group (particularly a 1-phenyl-5 -tetrazolylthio group) is introduced as a substituent into the benzoquinone nucleus. The other substituent, $R_1$, is an alkyl group or an alkylthio group. In this case, each alkyl group needs only provide the property to the DIR-hydroquinone by which the DIR-hydroquinone does not diffuse in hydrophilic colloid layers. For example, if the alkyl group has 6 or more carbon atoms, it has substantially such property. However, alkyl groups having 6 to 18 carbon atoms are preferred from an economic point of view.

Examples of di-substituted benzoquinones having the general formula (II) include 2-(1-phenyl-5-tetrazolylthio)-6-(1,1,3,3,-tetramethylbutyl)-p-benzoquinone, 2-n-octadecylthio-5-(1-phenyl-5-tetrazolylthio)-p-benzoquinone, 2-(1-phenyl-5-tetrazolylthio)-5-(1,1,3,3-tetramethylbutyl)-p-benzoquinone, 2-n-octyl-5-(1-phenyl-5-tetrazolylthio)-p-benzoquinone, 2-(1-phenyl-5-tetrazolylthio)-5-(1,1,3,3-tetramethylbutyl)-p-benzoquinone, 2-n-octadecylthio-6-(1-phenyl-5-tetrazolylthio)-p-benzoquinone, 2-n-octyl-6-(1-phenyl-5-tetrazolylthio)-p-benzoquinone, 2-n-hexadecyl-5-(1-phenyl-5-tetrazolylthio)-p-benzoquinone, 2-n-hexadecyl-6-(1-phenyl-5-tetrazolylthio)-p-benzoquinone, 2-n-pentadecyl-5-(1-phenyl-5-tetrazolylthio)-p-benzoquinone, 2-n-pentadecyl-6-(1-phenyl-5-tetrazolylthio)-p-benzoquinone and 2-n-octadecyl-5-(1-phenyl-5-tetrazolylthio)-p-benzoquinone, etc.

These di-substituted benzoquinone derivatives having the general formula (II) can be easily produced according to the processes described in U.S. Pat. Nos. 3,364,022, 3,639,417, etc. Further, they can be easily synthesized according to the following process. Namely, a 2-alkylthio-5(or -6)-(1-phenyl-5-tetrazolylthio) -p-benzoquinone is obtained by a process comprising reacting p-benzoquinone (2 mols) with an alkyl thiol compound (1 mol) in an organic solvent such as methanol, reacting the resulting p-benzoquinone substituted with an alkylthio group with 1-phenyl-5-mercaptotetrazole in an organic solvent, and oxidizing the reaction mixture with an oxidizing agent such as manganese dioxide or ferric chloride. Further, 2-alkyl-5(or -6)-(1-phenyl-5-tetrazolylthio)-p-benzoquinone can be obtained by a process comprising oxidizing a 2-alkylhydroquinone with an oxidizing agent, reacting the resulting 2-alkyl-p-benzoquinone with 1-phenyl-5-mercaptotetrazole and oxidizing the resulting 2-alkyl-5(or -6)-(1-phenyl-5-tetrazolylthio)hydroquinone with an oxidizing agent.

On the other hand, the thiol compound having the general formula (III) can be chosen from known commercially available compounds. Examples of the thiol compound having the general formula (III) include thiophenol, thiosalicylic acid, methylthiosalicylate, ethylthiosalicylate, octylthiosalicylate, n-decylthiosalicylate, n-octadecylthiosalicylate, o-nitrothiophenol, p-nitrothiophenol, p-amylthiophenol, p-butylthiophenol, p-propylthiophenol, p-ethylthiophenol, o-thiocresol, m-thiocresol and p-thiocresol, etc. The substituents of the thiol compound represented by the above described general formula (III), alkyl is not limited and is able to vary in a wide range.

In the process described above, although the reaction of the di-substituted benzoquinone and the thiol compound can be carried out in equimolar amounts, it is preferred to use the thiol compound in an excess amount in order to prevent oxidation of the thiol compound. For example, the thiol compound is used in the amount of about 1 to 2 mols per mol of the di-substituted benzoquinone. From an economic standpoint, a suitable ratio is about 1 to 1.2 mols of the thiol compound per mol of the di-substituted benzoquinone. The reaction can be carried out in an organic solvent at about 0° to 150°C, preferably 0°to 80°C, for about 1 to 10 hours. Of course, the reaction time is not limited to a certain range, because it will vary depending upon the reaction temperature employed. Since the organic solvent is simply a reaction medium, any kind of organic solvent can be used with general factors such as hazardous characteristics and availability, etc., of the solvent being considered. Examples of suitable organic solvents include ethers such as diethyl ether, dioxane and tetrahydrofuran, alcohols such as methanol, ethanol and butanol, aromatic and halogenated aromatic hydrocarbons such as benzene, toluene, xylene, chlorobenzene and dichlorobenzene, alicyclic hydrocarbons such as n-hexane and n-octane, ketones such as acetone and methyl ethyl ketone, and halogenated hydrocarbons such as methylene chloride, carbon tetrachloride and chloroform. The reaction can generally be carried out under atmosphere pressure but an inert atmosphere such as nitrogen, helium, argon, etc. can be advantageously used in order to suppress any tendency toward oxidation of the products, if desired.

Thus, the novel tri-substituted hydroquinone compounds represented by the general formula (I) can be synthesized. Examples of tri-substituted hydroquinone compounds represented by the general formula (I) include 2-(1-phenyl-5-tetrazolylthio)-3-phenylthio-6-(1,1,3,3-tetramethylbutyl)hydroquinone, 2-n-octadecylthio-5-(1-phenyl-5-tetrazolylthio)-6-phenylthiohydroquinone, 2-[2,5-dihydroxy-6-(1-phenyl-5-tetrazolylthio)-3-(1,1,3, 3-tetramethylbutyl)]-phenylthiobenzoic acid, methyl-2-[2,5-dihydroxy-3-n-octadecylthio-6-(1-phenyl-5-tetrazolylthio)] phenylthiobenzonate, 2-[2,5-dihydroxy-6-(1-phenyl-5-tetrazolylthio)-4-(1,1,3,3-tetramethylbutyl)]-phenylthiobenzoic acid, 2-(1-phenyl-5-tetrazolylthio)-3-phenylthio-5-(1,1,3,3-tetramethylbutyl)-hydroquinone, 2-[2,5-dihydroxy-3-n-hexadecylthio-6-(1-phenyl-5-tetrazolylthio)]-phenylthiobenzoic acid, 2-n-hexadecylthio-5-(1-phenyl-5-tetrazolylthio)-6-phenylthiohydroquinone, 2-p-methylphenylthio-6-n-octadecylthio-3-(1-phenyl-5-tetrazolylthio)-hydroquinone, 2-o-methylphenylthio- 3-(1-phenyl-5-tetrazolylthio)-6-(1,1,3,3-tetramethylbutyl)-hydroquinone, 2-p-nitrophenylthio-3-(1-phenyl-5-tetrazolylthio)-6-(1,1,3,3-tetramethylbutyl)-hydroquinone, 2-(1-phenyl-5-tetrazolylthio)-3-(p-propylphenylthio)-5-n-octadecylthiohydroquinone, n-octadecyl-2-[2,5-dihydroxyl-3-n-hexadecylthio-6-(1-phenyl-5-tetrazolylthio)]-phenylthiobenzoate, 2-(p-amylphenylthio)-6-n-hexadecylthio-3-(1-phenyl-5-tetrazolylthio)-hydroquinone, etc.

The tri-substituted hydroquinone compounds of the present invention can be added to photographic layers of color photographic sensitive materials (for example, silver halide emulsion layers) in the same manner as the above described prior art. The tri-substituted hydroquinone compounds have the characteristic that they have a 1-phenyl-5-tetrazolylthio group and at least one thioether group. The compounds of the present invention are superior to known compounds having only a 1-phenyl-5-tetrazolylthio group because of the characteristics they provide, that is, the sharpness, granularity and color reproduction of the images formed on silver halide photographic sensitive materials are remarkably improved and storability of photographic sensitive materials is improved, too.

The following examples are given to illustrate the present invention in greater detail. Unless otherwise indicated, all parts, percents, ratios and the like are by weight.

EXAMPLE 1

15g of 2-(1-phenyl-5-tetrazolylthio)-6-(1,1,3,3-tetramethylbutyl)-p-benzoquinone was added to 150ml of methanol and the mixture was cooled to 0°C while stirring. Then a solution of 4.5g of thiophenol in 25ml of methanol was added dropwise to this mixture. After the addition, the mixture was stirred at 0°C for 3 hours. The resulting crystals were separated by filtration and recrystallized from a solvent mixture of n-hexane and ethyl acetate (n-hexane/ethyl acetate = 5/1 by volume). Thus 7.5g of 2-(1-phenyl-5-tetrazolylthio)-3-phenylthio-6-(1,1,3,3-tetramethylbutyl)-hydroquinone having a melting point of 147°C was obtained.

Elemental Analysis

| | C | H | N |
|---|---|---|---|
| Calculated for $C_{27}H_{30}N_4O_2S_2$ (%) | 64.02 | 5.97 | 11.06 |
| Found (%) | 64.18 | 5.96 | 11.16 |

EXAMPLE 2

50g of 2-n-octadecylthio-5-(1-phenyl-5-tetrazolylthio)-p-benzoquinone was added to 1 liter of benzene. After adding 11g of thiophenol to this mixture, the mixture was stirred at 20°C for 6 hours. Then benzene was removed by distillation under a reduced pressure, and the resulting crystals were separated by filtration and washed with water. They were recrystallized form n-hexane. Thus 40g of needle-like crystals of 2-n-octadecylthio-5-(1-phenyl-5-tetrazolylthio)-6-phenylthiohydroquinone having a melting point of 96°C was obtained.

Elemental Analysis

| | C | H | N |
|---|---|---|---|
| Calculated for $C_{37}H_{50}N_4O_2S_3$ (%) | 65.46 | 7.42 | 8.25 |
| Found (%) | 65.64 | 7.37 | 8.34 |

The infrared absorption spectrum of the resulting 2-n-octadecylthio-5-(1-phenyl-5-tetrazolylthio)-6-phenylthiohydroquinone is shown in FIG. 1.

EXAMPLE 3

17g of 2-(1-phenyl-5-tetrazolylthio)-5-(1,1,3,3-tetramethylbutyl)-p-benzoquinone was added to 200ml of methanol and stirred at 20°C. A solution of 6.8g of thiosalicyclic acid in 50ml of methanol was added dropwise to this mixture at 20°C. After the addition, the mixture was stirred at 20°C for 3 hours. Methanol was removed from the reaction solution by distillation under a reduced pressure, and 50ml of benzene was added thereto to obtain crystals. The resulting crystals were separated by filtration and recrystallized from a solvent mixture of ethyl acetate and n-hexane (n-hexane/ethyl acetate = 5/1 by volume). Thus, 5g of 2-[2,5-dihydroxy-6-(1-phenyl-5-tetrazolylthio)-3-(1,1,3,3-tetramethylbutyl)]-phenylthiobenzoic acid having a decomposition point of 183°–184°C was obtained.

Elemental Analysis

| | C | H | N |
|---|---|---|---|
| Calculated for $C_{28}H_{30}N_4O_4S_2$ (%) | 61.08 | 5.49 | 10.18 |
| Found (%) | 61.32 | 5.51 | 10.15 |

EXAMPLE 4

15g of 2-n-octadecylthio-5-(1-phenyl-5-tetrazolylthio)-p-benzoquinone and 5g of methylthiosalicylate were added to 200ml of methanol and the mixture was refluxed for 3 hours with heating. After removing the methanol from the reaction mixture by distillation under a reduced pressure, 500ml of n-hexane was added thereto to precipitate crystals. The resulting crystals were separated by filtration at 20°C and recrystallized from a solvent mixture of n-hexane and ethyl acetate (n-hexane/ethyl acetate = 5/1 by volume). Thus, 5g of methyl-2-[2,5-dipydroxy-3-n-octadecylthio-6-(6-phenyl-5-tetrazolylthio)]-phenylthiobenzoate having a melting point of 123°C was obtained. The infrared absorption spectrum of this compound is shown in FIG. 2.

Elemental Analysis

| | C | H | N |
|---|---|---|---|
| Calculated for $C_{39}H_{52}N_4O_4S_3$ (%) | 63.57 | 7.11 | 7.60 |
| Found (%) | 63.55 | 7.13 | 7.51 |

EXAMPLE 5

7.2g of 2-(1-phenyl-5-tetrazolylthio)-5-(1,1,3,3-tetramethylbutyl)-p-benzoquinone and 3g of p-nitrothiophenol were added to 250ml of methanol and the mixture was stirred at 20°C for 8 hours. Methanol was removed from the reaction solution by distillation under a reduced pressure, and 50ml of n-hexane was added thereto to obtain crystals. The resulting crystals were separated by filtration and re-crystallized from a solvent mixture of n-hexane and ethyl acetate (n-hexane/ethyl acetate = 5/1 by volume). Thus, 5.1g of 2-p-nitrophenylthio-3-(1-phenyl-5-tetrazolylthio)-6-(1,1,3,3-tetramethylbutyl)-hydroquinone having a decomposition point of 173°–174°C.

| Elemental Analysis | C | H | N |
|---|---|---|---|
| Calculated for $C_{27}H_{29}N_5O_4S_2$ (%) | 58.80 | 5.26 | 12.70 |
| Found (%) | 59.18 | 5.40 | 12.80 |

While the invention has been described in detail and with reference to specific embodiments thereof, it will be apparent to one skilled in the art that various changes and modifications can be made therein without departing from the spirit and scope thereof.

What is claimed is:

1. A tri-substituted hydroquinone compound having the general formula (I)

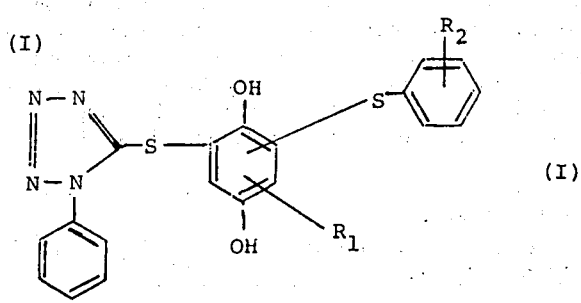

(I)

wherein $R_1$ represents an alkyl group having 6 to 18 carbon atoms or an alkylthio group having 6 to 18 carbon atoms; and $R_2$ represents a hydrogen atom, an alkyl group having 1 to 5 carbon atoms, a nitro group, a carboxylic acid group or an alkoxycarbonyl group having 1 to 18 carbon atoms in the alkoxy moiety thereof.

2. The hydroquinone compound of claim 1, wherein said hydroquinone compound is 2-(1-phenyl-5-tetrazolylthio)-3-phenylthio-6-(1,1,3,3-tetramethylbutyl)hydroquinone, 2-n-octadecylthio-5-(1-phenyl-5-tetrazolylthio)-6-phenylthiohydroquinone, 2-[2,5-dihydroxy-6-(1-phenyl-5-tetrazolylthio)-3-(1,1,3,3-tetramethylbutyl)]phenylthiobenzoic acid, methyl-2-[2,5-dihydroxy-3-n-octadecylthio-6-(1-phenyl-5-tetrazolylthio)]phenylthiobenzoate, 2-[2,5-dihydrozy-6-(1-phenyl-5-tetrazolylthio)-4-(1,1,3,3-tetramethylbutyl)]phenylthiobenzoic acid, 2-(1-phenyl-5-tetrazolylthio)-3-phenylthio-5-(1,1,3,3-tetramethylbutyl)hydroquinone, 2-[2,5-dihydroxy-3-n-hexadecylthiio-6-(1-phenyl-5-tetrazolylthio)]phenylthiobenzoic acid, 2-n-hexadecylthio-5-(1-phenyl-5-tetrazolylthio)-6-phenylthiohydroquinone, 2-p-methylphenylthio-6-n-octadecylthio-3-(1-phenyl-5-tetrazolylthio)hydroquinone, 2-o-methylphenylthio-3-(1-phenyl-5-tetrazolylthio)-6-(1,1,3,3-tetramethylbutyl)hydroquinone, 2-p-nitrophenylthio-3-(1-phenyl-5-tetrazolylthio)-6-(1,1,3,3-tetramethylbutyl)hydroquinone, 2-(1-phenyl-5-tetrazolylthio)-3-(p-propylphenylthio)-5-n-octadecylthiohydroquinone, n-octadecyl-2-[2,5-dihydroxyl-3-n-hexadecylthio-6-(1-phenyl-5-tetrazolylthio)] phenylthiobenzoate or 2-(p-amylphenylthio)-6-n-hexadecylthio-3-(1-phenyl-5-tetrazolylthio)hydroquinone.

3. The hydroquinone compound of claim 1, wherein said hydroquinone compound is 2-(1-phenyl-5-tetrazolylthio)-3-phenylthio-6-(1,1,3,3-tetramethylbutyl)hydroquinone, 2-n-octadecylthio-5-(1-phenyl-5-tetrazolylthio)-6-phenylthiohydroquinone, 2-[2,5-dihydroxy-6-(1-phenyl-5-tetrazol-ylthio)-3-(1,1,3,3-tetramethylbutyl)]-phenylthiobenzoic acid methyl-2-[2,5-dihydroxy-3-n-octadecylthio-6-(1-phenyl-5-tetrazolylthio)]phenylthiobenzoate or 2-p-nitrophenylthio-3-(1-phenyl-5-tetrazolylthio)-6-(1,1,3,3-tetramethylbutyl)hydroquinone.

* * * * *